United States Patent [19]

Nishikawa et al.

[11] Patent Number: 5,190,822
[45] Date of Patent: Mar. 2, 1993

[54] SURFACE-MODIFIABLE LIPOSOME AND PROCESS FOR PRODUCING SURFACE-MODIFIED LIPOSOME

[75] Inventors: Naoyuki Nishikawa; Mitsunori Ono, both of Kanagawa, Japan

[73] Assignee: Fuji Photo Film Co., Ltd., Kanagawa, Japan

[21] Appl. No.: 687,799

[22] Filed: Apr. 19, 1991

[30] Foreign Application Priority Data

Apr. 20, 1990 [JP] Japan .................. 2-104670
Aug. 17, 1990 [JP] Japan .................. 2-216750

[51] Int. Cl.⁵ .................. A61K 9/127; B01J 13/20
[52] U.S. Cl. .................. 428/402.2; 264/4.1; 264/4.3; 264/4.6; 424/450; 436/829; 514/78
[58] Field of Search .................. 264/4.1, 4.3, 4.6; 428/402.2; 424/450; 436/829; 514/78

[56] References Cited

U.S. PATENT DOCUMENTS

| | | | |
|---|---|---|---|
| 4,429,008 | 1/1984 | Martin et al. | 428/402.2 |
| 4,480,041 | 10/1984 | Myles et al. | 436/829 X |
| 4,603,044 | 7/1986 | Geho et al. | 428/402.2 X |
| 4,605,630 | 8/1986 | Kung et al. | 428/402.2 X |
| 4,762,915 | 8/1988 | Kung et al. | 424/450 X |
| 4,791,207 | 12/1988 | Salzmann et al. | 548/110 |
| 4,808,480 | 2/1989 | Regen | 428/402.2 |
| 4,861,597 | 8/1989 | Kida et al. | 424/450 |
| 5,000,960 | 3/1991 | Wallach | 424/450 |

*Primary Examiner*—Richard D. Lovering
*Attorney, Agent, or Firm*—Sughrue, Mion, Zinn, Macpeak & Seas

[57] ABSTRACT

A surface-modifiable liposome comprising a compound represented by formula (I) or (II):

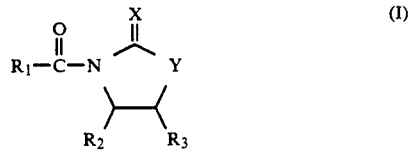

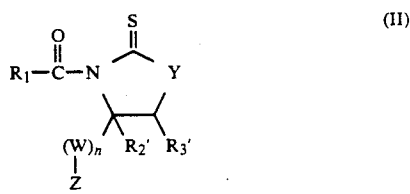

and a lipid capable of forming a liposome, wherein
$R_1$ represents a hydrophobic group;
$R_2$ and $R_3$ represent each an organic group including a hydrogen atom) $R_2$ and $R_3$ optionally combined with each other to form a double bond or a ring;
X and Y each represents an oxygen atom or a sulfur atom; $R_2'$ and $R_3'$ each represents a hydrogen atom or an organic group; W represents a linking group; n represents 0 or 1; and Z represents a hydrophilic group;

and a process for producing a surface-modified liposome by using the surface-modifiable liposome.

11 Claims, 1 Drawing Sheet

SURFACE-MODIFIABLE LIPOSOME AND PROCESS FOR PRODUCING SURFACE-MODIFIED LIPOSOME

FIELD OF THE INVENTION

This invention relates to a surface-modifiable liposome which is useful as, for example, a drug carrier or a reagent for immunological analysis and a process for producing a surface-modified liposome.

BACKGROUND OF THE INVENTION

Recently, a drug delivery system (DDS), whereby a drug is transported selectively toward the cells or tissue in the target part and then the medical effect of the drug is expressed therein without affecting normal cells or tissues, has been discussed in the fields of medicine and pharmacology.

In order to achieve this object, attempts have been made to produce a surface-modified liposome carrying a hydrophilic or fat-soluble drug, on the surface of which a substrate (for example, protein, antigen, antibody, saccharide including polysaccharide) is fixed (e.g., as disclosed in Cancer Res., 43, 5328 (1983); ibid., 47, 4471 (1987); and Liposome Res., 1, 15 (1988–89))

However liposomes are disadvantageous in that they are unstable and thus rapidly disappear in the presence of phagocytes in the reticuloendothelial system or from blood when administered to a living organism. In order to solve these problems, JP-A-63-313724 has disclosed a method for modifying the surface of a liposome with a polysaccharide derivative (the term "JP-A" as used herein means an "unexamined published Japanese patent application").

Furthermore, a number of analytical methods with the use of surface-modified liposomes, which are obtained by fixing physiologically active substances or immunologically active substances including antigens and antibodies on the surface of liposomes, have been disclosed in the fields of clinical research and diagnosis and immunology (e.g., as disclosed in JP-A-61-250558; JP-A-61-66963; and JP-A-60-138466).

Typical examples of methods for modifying the surface of liposomes include a method comprising binding a protein activated with N-succinimidyl-3-(2-pyridyldithio) propionate (SPDP) to N-3-(2-dithiopyridyl) propionyl phosphatidylethanolamine (DTP-PE) (e.g., as disclosed in Nature, 288, 602 (1980)) and another method comprising a cross-linking agent (for example, N-succinimidyl-4-(p-maleimidophenyl) butyrate (SMPB), N-succinimidyl-4-(p-maleimidophenyl)acetate (SMPA), N-succinimidyl-4-(p-maleimidophenyl)propionate (SMPP)) (e.g., as disclosed in J. Biol. Chem., 257, 286 (1982))

Furthermore, other methods for fixing a substrate on the surface of liposomes, have been represented, for example, one comprising preliminarily adding a glycolipid in the preparation of liposomes, then oxidizing the saccharide of the glycolipid to thereby form an aldehyde group and reacting the aldehyde group with an amino group of, for example, a protein to thereby form a Schiff base (refer to Biochim. Biophys. Act., 640, 66 (1981)) and one comprising introducing a hydrophobic group into a substrate, for example, a protein and then integrating it into liposomes which have been separately prepared (e.g., as disclosed in Biochim. Biophys. Act., 812, 116 (1985))

However each of these methods comprises many steps and requires complicated procedures. Thus, there has been a long-standing need in the art to establish a convenient process for easily fixing a substrate on the surface of a liposome to thereby modify the liposome.

In the field of organic synthetic chemistry, on the other hand, a method for efficiently producing an aldehyde by reducing a carboxylic acid derivative with the use of 3-acylthiazolidine-2-thione has been disclosed (e.g., as disclosed in JP-A-54-79275; and Chem. Lett., 1443 (1977)), one selectively producing an amide (e.g., as disclosed in Tetrahedron Lett., 21, 841 (1980); and Hetero cycles, 77, 537 (1982)) and one for producing a thioester (e.g., as disclosed in J. Chem. Research(S), p.20 (1983)). However, there has never been reported hitherto use of 3-acylthiazolidine-2-thione as a reagent for modifying the surface of a liposome.

In the field of polymeric chemistry, furthermore, there has been reported an activator having 2(3H)-benzoxazolone or 2(3H)-benzothiazolone as an eliminating group which selectively forms an amide (e.g., as disclosed in Yuki Gosei Kagaku Kyokai Shi, 48, 144 (1989); Bull. Chem. Soc. Jpn., 58, 3291 (1985); and Macromolecules, 18, 2353 (1985)).

SUMMARY OF THE INVENTION

So far, the use of amide compounds having an eliminating group as a reagent for modifying the surface of a liposome has not been reported.

Accordingly, it is an object of the present invention to solve the aforesaid problems of known methods for producing liposomes by providing a process for easily producing a surface-modified liposome on which various substrates (for example, peptides including amino acids, proteins including antigens and antibodies, saccharides including polysaccharides) are fixed and a surface-modifiable liposome on the surface of which various substrates can be fixed.

The above-mentioned object of the present invention has been achieved by providing:

(1) a surface-modifiable liposome comprising a compound represented by formula (I) or (II):

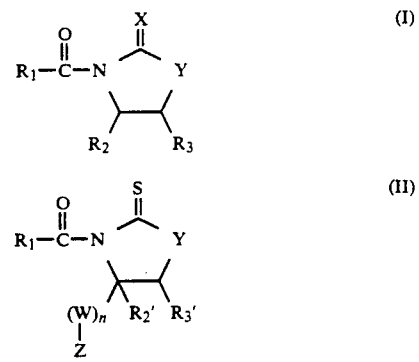

and a lipid capable of forming a liposome; wherein
$R_1$ represents a hydrophobic group;
$R_2$ and $R_3$ each represents an organic group or a hydrogen atom; $R_2$ and $R_3$ optionally are bound to each other to form a double bond or a ring; X and Y each represents an oxygen atom or a sulfur atom;
$R_2'$ and $R_3'$ each represents a hydrogen atom or an organic group; W represents a linking group;
n represents 0 or 1; and Z represents a hydrophilic group.

(2) a process for producing a surface-modified liposome comprising mixing a surface-modifiable liposome as described in (1) above with a substrate having an amino group and/or a thiol group; and (3) a process for producing a surface-modified liposome comprising mixing a substrate derivative comprising at least one compound represented by formula (I) or (II) as described in (1) above bound to a substrate having at least one of an amino group and a thiol group, with a lipid capable of forming a liposome.

Accordingly the present invention provides for fixing a substrate having an amino group or a thiol group on the surface of a liposome by using a liposome in a bilayer membrane of which a long-chain active amide represented by formula (I) or (II) is embedded; and forming a liposome by reacting a long-chain active amide represented by formula (I) or (II) with a substrate having an amino group or a thiol group to obtain a substrate derivative having a long-chain group and then mixing the substrate derivative with a lipid capable of forming a liposome.

DETAILED DESCRIPTION OF THE INVENTION

Figure 1:
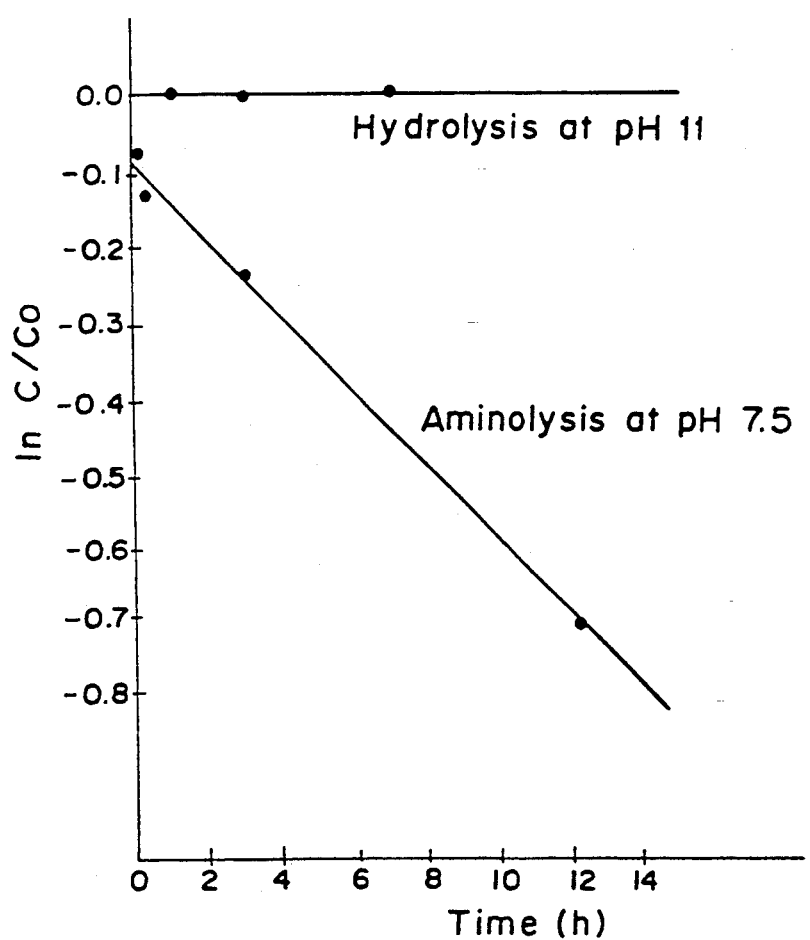
FIG. 1 shows a plot of ln C/Co (ln concentration/original concentration) of a long-chain active amide I-1 (in formula (I), $R_1 = C_{17}H_{35}$, $R_2 = R_3 = H$, $X = Y = S$) embedded in liposome membrane against time.

The processes for providing surface-modified liposomes of the present invention is described below.

A first process according to the present invention comprises mixing a long-chain active amide represented by formula (I) or (II) with at least one compound capable of forming liposomes to thereby produce liposomes. As the material capable of forming liposomes to be used in the first process of the present invention, lipids employed in known methods for producing liposomes, except phosphatidylethanolamine and phosphatidylserine, can be used. Examples of lipids that can be used according to the present invention include at least one of lecithins such as yolk lecithin and soybean lecithin, dipalmitoylphosphatidylcholine (DPPC), dimyristoylphosphatidylcholine (DMPC), distearoylphosphatidylcholine (DSPC), dioleylphosphatidylcholine (DOPC), dipalmitoylphosphatidylglycerol (DPPG) and dimyristorylphosphatidic acid (DMPA).

Either one or more lipids selected from the above-mentioned ones may be used. Further, these lipids may be used in the form of a mixture together with cholesterols. Furthermore, a mixture comprising substances other than lipids or cholesterols may be used.

In the first process of the present invention, the molar ratio of the long-chain active amide, represented by formula (I) or (II), to the whole of the materials capable of forming liposomes can be arbitrarily selected over a wide range so long as liposomes can be formed. It is preferable that the molar ratio is from 1 to 50%, more preferably from 5 to 35%.

In the first process for producing liposomes of the present invention, liposomes may be produced by known methods, for example, a vortexing method, an ultrasonic method, a surfactant-removal method, a reverse phase evaporation method (REV method), an ethanol-injection method, an ether-injection method, a prevesicle method, a French press method, an extrusion method, an annealing method, a freezing/melting method, a W/O/W emulsion method, a stable plurilamellar vesicle method (SPLV method) (e.g., as disclosed in Biochemistry, 25, 2833 (1985))

Such methods for producing liposomes are summarized by Papahadjopoulos et al. (Ann. Rev. Biophys. Bioeng., 9, 467 (1980)) and described by Nojima, Sunamoto, Inoue, et al. ("liposome", pp. 21-40, Nankodo (1988)), the contents of which are herein incorporated by reference.

Examples of compounds to be encapsulated within liposomes produced by the first process of the present invention include but are not limited to, drugs, antibiotics, pigments and fluorescent substances.

Surface-modified liposomes, on which a substrate is fixed, may be produced by adding a substrate having at least one of an amino group and a thiol group or a solution of said substrate to the dispersion of the surface-modifiable liposomes obtained above, followed by allowing the mixture to stand or be shaken until the surface modified liposome is founded.

The substrate to be fixed in the first process of the present invention is not particularly restricted so long as it has at least one of an amino group and a thiol group. A substrate having an amino group is preferable. Examples of such substrates include peptides (including amino acids such as physiologically active peptides (for example, oxytocin, vasopressin, thyrotropin-releasing hormone (TRH)) and other hormones; proteins including antigens such as immunoglobulins (for example, IgG, IgE, IgM), carcinoembryonic antigen (CEA), pancreatinc carcinoembryonic antigen (POA), antibodies such as β-fetoprotein monoclonal antibody, immunoglobulin monoclonal antibody and other proteins such as bovine serum albumin (BSA); and saccharides including polysaccharides such as glucosamine and galactosamine.

In a first process of the present invention, surface-modifiable or surface-modified liposomes may be purified by known methods, for example, by gel filtration with the use of a Sephadex TM or Sepharose TM column, by centrifugation or by dialysis.

The second process of the present invention comprises mixing a substrate, having an amino group or a thiol group described in the first process of the present invention, with a long-chain active amide represented by formula (I) or (II) in an organic solvent, water or a buffer solution to thereby obtain a substrate derivative having a long-chain group, followed by purifying the derivative thus obtained and then mixing it with a material capable of forming liposomes to thereby produce liposomes of the present invention.

Materials capable of forming liposomes in the second process of the present invention additional to those described above for the first process, include, e.g., phosphatidylethanolamine and phosphatidylserine. In the second process of the present invention, the molar ratio of materials capable of forming liposome to the substrate derivative having a long-chain group can be arbitrarily selected over a wide range so long as liposomes can be formed. The molar ratio is preferably from 1 to 50%, more preferably from 5 to 35%.

In the second process of the present invention, methods for producing liposomes, compounds to be encapsulated within the liposomes, substrates to be fixed on the liposomes and methods for purifying the liposomes are each the same as those employed in the first process of the present invention.

Furthermore, in the second process of the present invention, substrate derivatives having a long-chain group can be used without performing any unification, for some methods for producing the liposomes. Further, water or a buffer solution containing the substrate derivative can be used as a liposome dispersion.

In long-chain active amides represented by formula (I) or (II), to be used in the present invention, $R_1$ represents a hydrophobic group. $R_1$ may be either a single-chain group or a double-chain group. $R_1$ having a single-chain group may be straight-chain or branched chain. Further, $R_1$ may be either saturated or unsaturated and optionally have substituent(s). $R_1$ may have cholesterol as hydrophobic groups. Examples of $R_1$ which are double-chain hydrophobic groups include those represented by the following formulae:

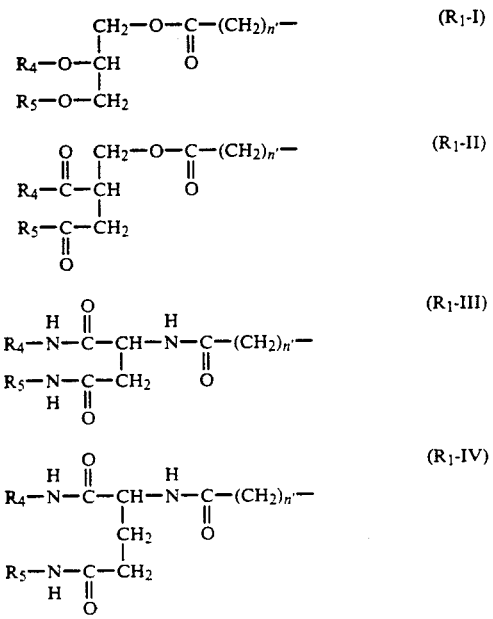

wherein $R_4$ and $R_5$ each represents an alkyl group having 1 to 22 carbon atoms which is either straight-chain or branched chain, either saturated or unsaturated and optionally is substituted; $n'$ is from 1 to 3; and the compound may be either optically active or racemic as to the chiral carbon atom.

When $R_1$ is a single-chain hydrophobic group, a straight-chain alkyl group having 8 or more, still preferably 12 or more, carbon atoms is preferable.

When $R_1$ is a double-chain hydrophobic group, a straight-chain alkyl group wherein $R_4$ and $R_5$ have both 8 or more, still preferably 12 or more, carbon atoms is preferable.

In long-chain active amides represented by formula (I), $R_2$ and $R_3$ each represents an organic group or a hydrogen atom. Further, $R_2$ and $R_3$ can combine with each other to thereby form a ring (for example, a saturated hydrocarbon ring, a saturated hetero-ring, an aromatic ring including are aromatic hetero-ring) or a double bond. Examples of $R_2$ and $R_3$ include H, $-CH_3$, $-CH_2CH_3$, $-OH$, $-COOH$, $-COOCH_3$, $-CH_2-OH$, $-CH_2-COOH$, $-CH_2-COOCH_3$, $-N^+H_3$, $-N^+(CH_3)_3$, $-CH_2-N^+H_3$, $-CH_2-N^+(CH_3)_3$, $-SO_3^-$ and $-CH_2-SO_3^-$. Among these groups, those having a hydrogen atom, $-OH$, $-COOH$, $-N^+(CH_3)_3$, or $-SO_3^-$ are preferred.

X and Y represent each O or S. It is preferable that both of X and Y are S.

$R_2'$ and $R_3'$ in formula (II) each represents a hydrogen atom or an organic group and preferably represents a hydrogen atom, an alkyl group, which may be bonded to the carbon atom constituting the ring through at least one oxygen atom, sulfur atom or $NR_6$ (wherein $R_6$ represents a hydrogen atom, an alkyl group, a cycloalkyl group, an aryl group, or an alkenyl group.), a cycloalkyl group, an alkenyl group, an alkynyl group, an alkyl group having 1 to 5 carbon atoms which is substituted by 1 to 3 halogen atoms, a cyano group, a halogen atom, a nitro group, an alkoxy group, an alkenoxy group, an alkynoxy group, an aryloxy group, an alkoxycarbonyl group, an aryloxycarbonyl group, an alkoxycarbonylthio group, an alkoxycarbonylamino group, a dialkylamino group, an alkylcarbonylamino group, an alkylcarbonyl group, a carbamoyl group, an alkylaminocarbonylamino group, an alkylaminocarbonyloxy group, an alkyl-aminocarbonylthio group, an alkylsulfinyl group, an arylsulfonyl group or an alkylthio group.

Z in formula (II) represents a hydrophilic group and preferably represents a dialkylamino group, a trialkylammonium group, a sulfo group or dissociated form thereof (wherein the alkyl group is preferably a methyl group, an ethyl group, or a propyl group. The counter anion of the ammonium group is preferably $I^-$, $BF_4^-$, $p$-$TsO^-$, $CH_3SO_3^-$, or $CH_3SO_4^-$. The countercation of the dissociated form of the sulfo group is preferably $Na^+$, $Li^+$ or $K^+$.

Y in formula (II) represents an oxygen atom or a sulfur atom and preferably represents a sulfur atom.

W in formula (II) represents a linking group and preferably represents $-(CH_2)_m-$, $-(CH_2)_m-CO-$, $-(CH_2)_m-SO_2-$, or

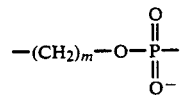

wherein m represents an integer of from 0 to 3.

n in formula (II) represents 0 or 1.

Long-chain active amides to be used according to the present invention may be synthesized by known methods, for example, those described in JP-A-54-79275; Tetrahedron Letters, 21, 841 (1980), Synthesis, (1982), 933; Maclomolecules, 21, 19 (1988).

Preferable examples of long-chain active amides represented by formula (I) in the present invention are as follows, although the present invention is not restricted thereby.

I-1

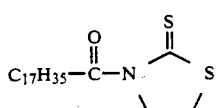

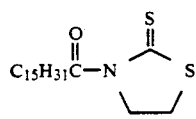
I-2
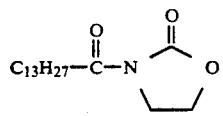
I-3
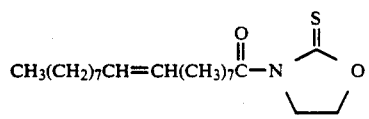
I-4
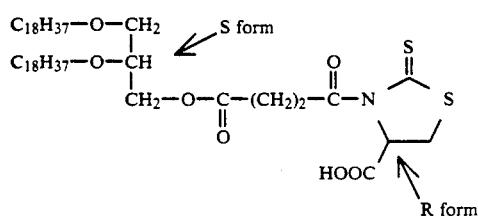
I-5
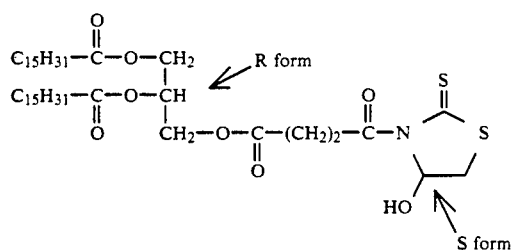
I-6
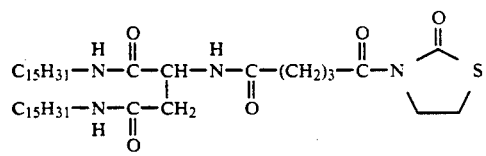
I-7
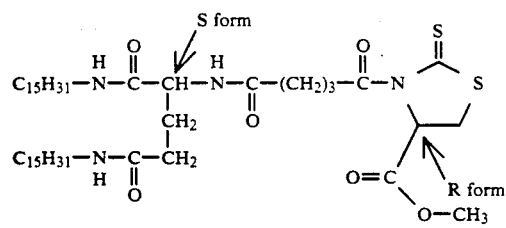
I-8
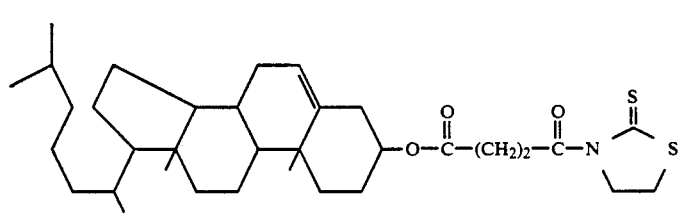
I-9
Preferable examples of long-chain active amides having a hydrophilic dissociative group represented by formula (II) in the present invention are as follows, although the present invention is not restricted thereby.

II-1 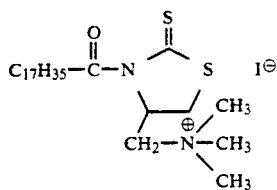 II-2 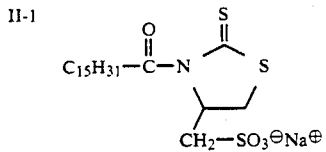
II-3 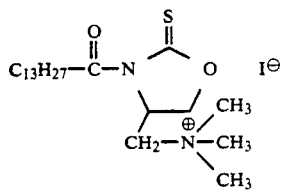 II-4 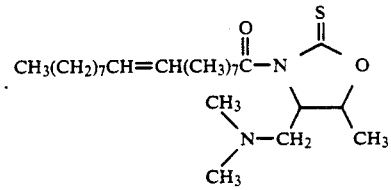
II-5 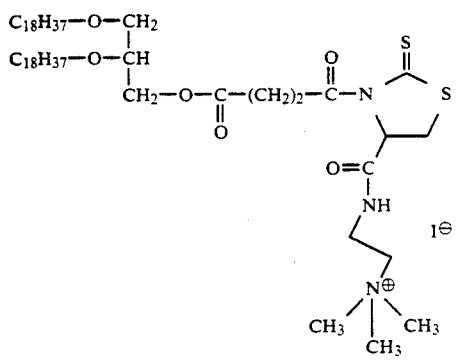 II-6 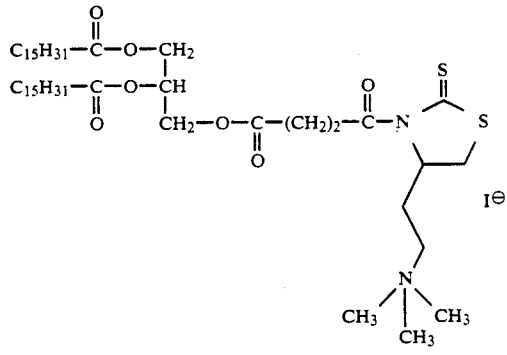
II-7 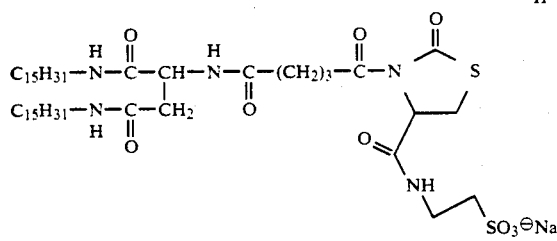 II-8 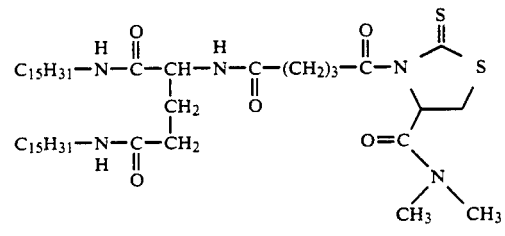
II-9 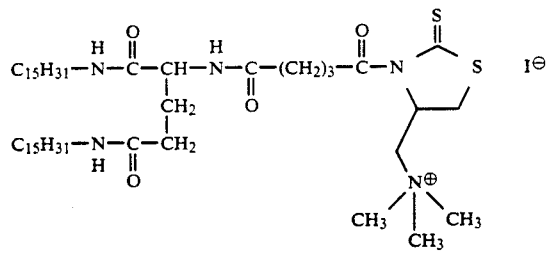
II-10 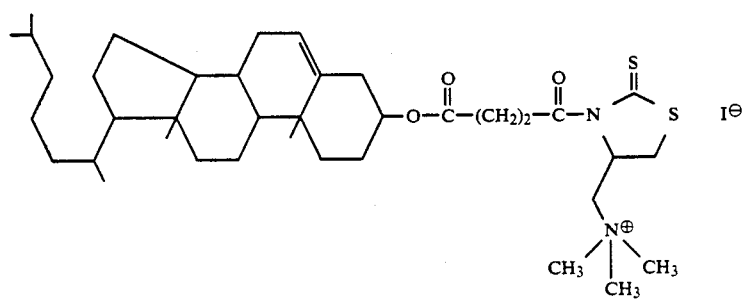

To further illustrate the present invention, and not by way of limitation, the following Synthetic Examples and Examples will be given.

SYNTHETIC EXAMPLE 1

Synthesis of Long-Chain Active Amide I-1 (in formula (I), $R_1=C_{17}H_{35}$, $R_2=R_3=H$, $X=Y=S$)

5.7 g of stearic acid was dissolved in 500 ml of dichloromethane and 4.0 g of dicyclohexyl carbodiimide (DCC) was added thereto followed by stirring. After 30 minutes, 2.2 g of 2-mercapto-2-thiazoline and 0.2 g of dimethylaminopyridine (DMAP) were added. After allowing to stand for a day and a night, the reaction mixture was filtered. Water was added to the filtrate and the organic phase was dried over mirabilite. After distilling off the dichloromethane under reduced pressure, the residue was purified by silica gel chromatography (eluent: hexane/ethyl acetate=8/2 by volume) and recrystallized from hexane. Thus 3.2 g of Long-Chain Active Amide I-1 (in formula (I), $R_1=C_{17}H_{35}$, $R_2=R_3=H$, $X=Y=S$) was obtained.

SYNTHETIC EXAMPLE 2

Synthesis of Long-Chain Active Amide I-3 (in formula (I), $R_1=C_{13}H_{27}$, $R_2=R_3=H$, $X=Y=O$)

The procedure of Synthetic Example 1 was repeated except that 4.6 g of myristic acid, 500 ml of dichloromethane, 1.75 g of 2-oxazolidone, 4.0 g of DCC and 0.2 g of DMAP were used. Thus 2.9 g of Long-Chain Active Amide I-3 (in formula (I), $R_1=C_{13}H_{27}$, $R_2=R_3=H$, $X=Y=O$) was obtained.

SYNTHETIC EXAMPLE 3

Synthesis of Long-Chain Active Amide I-8 (in formula (I)

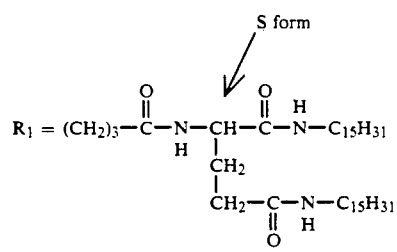

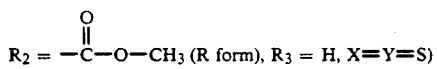

2.5 g of carbobenzoxy-l-glutamic acid was dissolved in 300 ml of tetrahydrofuran and 4.2 g of DCC was added thereto. Next, 4.8 g of cetylamine and 2.1 g of triethylamine (TEA) were added thereto and the mixture was allowed to stand for a day and a night. After distilling off the solvent under reduced pressure, the residue was dissolved in chloroform and the organic phase was washed with water and dried over mirabilite. After distilling off the chloroform, the residue was purified by silica gel chromatography (eluent: hexane/ethyl acetate=8/2 by volume). Thus 4.3 g of a dialkylamide product was obtained. This product was then dissolved in ethyl acetate and hydrolyzed with 1.0 g of 5% palladium carbon for 5 hours. The reaction mixture was filtered through celite and the ethyl acetate was distilled off from the filtrate under reduced pressure. Thus 3.4 g of an amine product (II) was obtained.

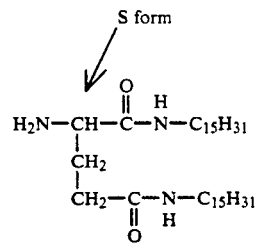

Then 1.0 g of glutaric anhydride was dissolved in THF. To the solution obtained, was added dropwise 100 ml of a solution of 3.4 g of the amine product (II) and 0.6 g of TEA in chloroform. After 2 hours, the solvent was distilled off under reduced pressure and chloroform was added. The organic phase was washed with diluted hydrochloric acid (aqueous phase: pH 3 to 4) and then dried over mirabilite. After distilling off the chloroform under reduced pressure, the residue was dissolved in 200 ml of dichloromethane. Then 1.3 g of DCC was added and the mixture was stirred for 30 minutes. 1.0 g of 4(R)-methoxycarbonyl-2-mercapto-2-thiazoline and 0.1 g of DAMP were added and the mixture was allowed to stand overnight. Then the reaction mixture was filtered and the filtrate was washed with water. The organic phase was dried over mirabilite and the dichloromethane was distilled off under reduced pressure. The residue was purified by silica gel chromatography (eluent: hexane/ethyl acetate=6/4 by volume) to thereby given 2.3 g of the Long-Chain Active Amide I-8 (in formula (I),

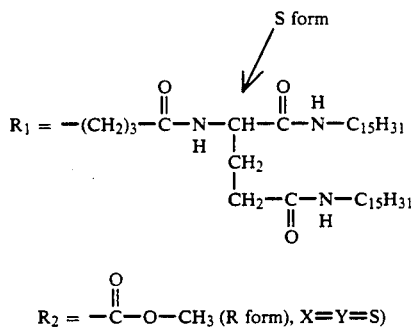

SYNTHETIC EXAMPLE 4

Synthesis of Long-Chain Active Amide II-1

5.7 g of stearic acid was dissolved in 500 ml of THF and 4.0 g of dicyclohexyl carbodiimide (DCC) was added thereto followed by stirring. After 30 minutes, 2.8 g of 3-(dimethylaminomethyl)-2-mercapto-2-thiazolizine and 0.2 g of dimethylaminopyridine (DMAP) were added. After allowing to stand for a day and a night, the reaction mixture was filtered and then the filtrate was concentrated. 10 ml of chloroform and 10 ml of methyliodido were added thereto and allowed to stand. Thus-generated crystals were removed by filtration and recrystallized from ether/ethanol to obtain 4.9 g of compound II-1.

SYNTHETIC EXAMPLE 5

Synthesis of Long-Chain Active Amide II-2

3.7 g of Long-Chain Active Amide II-2 was prepared in the same manner as in Synthetic Example 4 by using 4.8 g of parmitinic acid, 300 ml of dimethylformamide, 2.0 g of 3-sulfomethyl-2-mercapto-2-thiazorizine, 4.5 g of DCC and 0.2 g of DMAP.

SYNTHETIC EXAMPLE 6

Synthesis of Long-Chain Active Amide II-9

2.5 g of carbobenzoxy-l-glutamic acid was dissolved in 300 ml of tetrahydrofuran and 4.2 g of DCC was added thereto. Next, 4.8 g of cetylamine and 2.1 g of triethylamine (TEA) were added thereto and the mixture was allowed to stand over a day and a night. After distilling off the solvent under reduced pressure, the residue was dissolved in chloroform and the organic phase was washed with water and dried over mirabilite. After distilling off the chloroform, the residue was purified by silica gel chromatography (eluent: hexane/ethyl acetate=8/2 by volume). Thus 4.3 g of a dialkylamide product was obtained. This product was then dissolved in ethyl acetate and hydrolyzed with the use of 1.0 g of 5% palladium carbon for 5 hours. The reaction mixture was filtered through celite and the ethyl acetate was distilled off from the filtrate under reduced pressure. Thus 3.4 g of an amine product (III) was obtained.

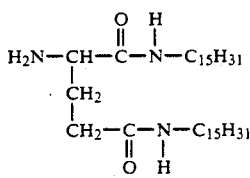

(III)

Then 1.0 g of glutaric anhydride was dissolved in THF. To the obtained solution, was added dropwise 100 ml of a solution of 3.4 g of the amine product (III) and 0.6 g of TEA in chloroform. After 2 hours, the solvent was distilled off under reduced pressure and chloroform was added. The organic phase was washed with diluted hydrochloric acid (aqueous phase: pH 3 to 4) and then dried over mirabilite. After distilling off the chloroform under reduced pressure, the residue was dissolved in 200 ml of THF. Then 1.3 g of DCC was added and the mixture was stirred for 30 minutes. 1.0 g of 3-dimethylaminomethyl-2-mercapto-2-thiazolizine and 0.1 g of DMAP were added and the mixture was allowed to stand overnight. Then the reaction mixture was filtered and then the filtrate was concentrated. The obtained mixture was dissolved in a mixture solvent of ether and chloroform and 3 ml of methyliodide was added thereto. The obtained crystals were recrystallized from ethanol/hexane to obtain 2.4 g of long-chain active amide II-9.

EXAMPLE 1

Process for producing surface-modifiable liposome 15 mg of DPPC and 2.3 mg of Long Chain Active Amide I-1 (in formula (I), $R_1=C_{17}H_{35}$, $R_2=R_3=H$, $X=Y=S$) were dissolved in 5 ml of chloroform. Next, the solvent was distilled off in a rotary evaporator to thereby form a film. The film was dried under reduced pressure and 0.5 ml of $H_2O$ was added thereto. Then it was allowed to stand in a water bath at 60° C. for 1 minute followed by shaking in a vortex mixer for 1 minute. After effecting this procedure thrice, the obtained dispersion was irradiated with ultrasonic waves with the use of a probe-type sonicator (25 W, 3 minutes). Then it was subjected to gel filtration with the use of a Sepharose 4B column to thereby give surface-modifiable liposomes (Tc: 41° C., average particle size: 560 nm).

EXAMPLE 2

Encapsulation test on surface-modifiable liposome

Similar to the procedure of Example 1, a dispersion was treated by using a 200 mM 5,(6)-carboxyfluorescein (5,(6)-CF) in a borate buffer solution (pH 8.5) to thereby prepare liposomes in which 5,(6)-CF was encapsulated (average particle size: 300 nm).

EXAMPLE 3

Process for producing surface-modifiable liposome and encapsulation test thereon 30 mg of DPPC and 2 mg of Long Chain Active Amide I-3 (in formula (I), $R_1=C_{13}H_{27}$, $R_2=R_3=H$, $X=Y=O$) were dissolved in 15 ml of chloroform. Then the procedure of Example 1 was repeated to thereby give surface-modifiable liposomes (Tc: 41° C., average particle size: 220 nm). Subsequently, liposomes in which 5,(6)-CF was encapsulated were prepared by using 200 mM 5,(6)-CF in a phosphate buffer solution (pH 7.4) (average particle size: 210 nm).

EXAMPLE 4

Process for producing surface-modifiable licosome and encapsulation test thereon 30 mg of Egg PC and 2 mg of Long-Chain Active Amide I-8 (in formula (I), $R_1 =$ 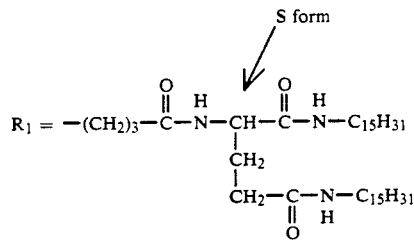

$R_2 =$

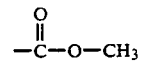

(R-form), $R_3=H$, $X=Y=S$) were dissolved in 15 ml of chloroform. Then the procedure of Example 1 was repeated to thereby give surface-modifiable liposomes (average particle size: 120 nm). Subsequently, liposomes in which 5,(6)-CF was encapsulated were prepared by the same method as the one described in Example 3.

EXAMPLE 5

Process for producing surface-modifiable liposome and encapsulation test thereon 30 mg of DPPC and 3 mg of Long-Chain Active Amide I-9 (in formula (I), $R_1 =$ -continued

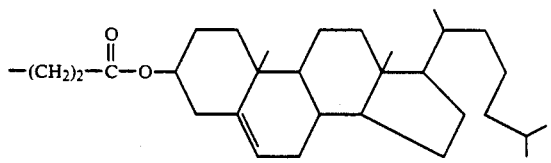

$R_2=R_3=H$, $X=Y=S$) were dissolved in 25 ml of chloroform. Then the procedure of Example 1 was repeated to thereby give surface-modifiable liposomes (average particle size: 150 nm). Subsequently, liposomes in which 5,(6)-CF was encapsulated were prepared by the same method as the one described in Example 3.

EXAMPLE 6

Process for producing benzylamine-fixed surface-modified liposome

To 0.4 ml of a dispersion of surface-modifiable liposomes in a phosphate buffer solution (pH 7.5), which was produced in the same manner as the one described in Example 1 by using Long-Chain Active Amide I-1 (in formula (I), $R_1=C_{17}H_{35}$, $R_2=R_3=H$, $X=Y=S$) (concentration: $4\times10^{-4}M$), was added 0.1 ml of a $4\times10^{-4}M$ benzylamine in a phosphate buffer solution (pH 7.5). Then the mixture was allowed to stand at 25° C. for 12 hours. As a result, benzylamine-fixed surface-modified liposomes on which benzylamine was fixed on 50% of the long-chain active amide (in formula (I), $R_1=C_{17}H_{35}$, $R_2=R_3=H$, $X=Y=S$) in the liposome membrane were obtained.

EXAMPLE 7

Process for producing peptide-fixed surface-modified liposome

To 0.4 ml of a dispersion of surface-modifiable liposomes in a phosphate buffer solution (pH 7.5), which was produced in the same manner as the one described in Example 6 by using Long-Chain Active Amide I-1 (in formula (I), $R_1=C_{17}H_{35}$, $R_2=R_3=H$, $X=Y=S$) (concentration: $4\times10^{-4}M$)), was added 0.1 ml of a $4\times10^{-2}M$ peptide (Gly-Ser-$\beta$-Ala) in a phosphate buffer solution (pH 7.5). Then the mixture was allowed to stand at 25° C. for 12 hours. As a result, peptide-fixed surface-modified liposomes on which said peptide (Gly-Ser-$\beta$-Ala) was fixed on 38% of the long-chain active amide I-1 (in formula (I), $R_1=C_{17}H_{35}$, $R_2=R_3=H$, $X=Y=S$) in the liposome membrane were obtained.

EXAMPLE 8

Process for producing protein-fixed surface-modified liposome

The procedure of Example 1 was repeated by using 15 mg of DPPC, 1.0 mg of Long-Chain Active Amide I-2 (in formula (I), $R_1=C_{15}H_{31}$, $R_2=R_3=H$, $X=Y=S$) and a PBS solution to thereby give surface-modifiable liposomes. These liposomes were sized with an extruder by using a micropore filter (0.2 μm) at 50° C. Then the dispersion was ultracentrifuged (10,000 rpm, 15 minutes) to thereby sediment the liposomes.

To the liposomes thus sedimented, was added 3 ml of a phosphate buffer solution. To a 1 ml portion of the mixture thus obtained, was added 1 ml of a 1 mg/ml human IgG solution in PBS followed by allowing it to stand at 25° C. for 12 hours. Then it was ultracentrifuged with the use of a PBS solution. Thus protein-fixed surface-modified liposomes, on which said protein (human IgG) was fixed, were obtained.

EXAMPLE 9

Process for producing peptide-fixed surface-modified liposome

To 1 ml of a dispersion of surface-modifiable liposomes in which Long-chain Active Amide I-8 (in formula (I),

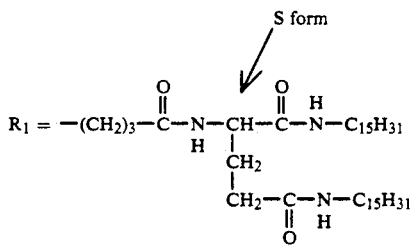

$R_2=$

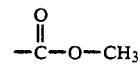

(R-form), $R_3=H$, $X=Y=S$) prepared in the same manner as the one described in Example 4, was embedded, was added 1 ml of an aqueous solution of a peptide (Gly-Ser-$\beta$-Ala) followed by allowing to stand at 25° C. for 12 hours. Then the liposome faction was collected by gel filtration to thereby give liposomes on which said peptide (Gly-Ser-$\beta$-Ala) was fixed were obtained.

EXAMPLE 10

Production of saccharide-fixed modified liposomes

In accordance with a method reported by Nagao et al. (Tetrahedron Lett., 21, 841 (1980)), N-tetradecanoyl glucosamine (III) was obtained.

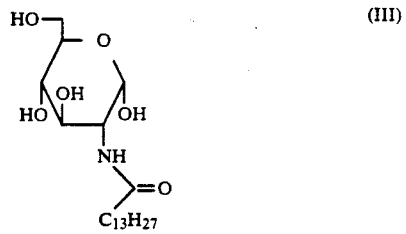

1 mg of N-tetradecanoyl glucosamine and 15 mg of DPPC were dissolved in 5 ml of a solvent mixture (methanol/chloroform=1/1 by volume). Next, the solvent was distilled with a rotary evaporator and thus a film was formed. After drying under reduced pressure, 3 ml of a PBS solution was added to the film. Then it was allowed to stand in a water bath at 60° C. for 1 minute followed by shaking in a vortex mixer for 1 minute. After effecting this procedure thrice, the obtained dispersion was irradiated with ultrasonic waves with the use of a probe-type sonicator (25 W, 10 minutes). Then it was subjected to gel filtration with the use of a Sepharose 4B column to thereby give modified liposomes on which said saccharide (glucosamine) was fixed.

EXAMPLE 11

Observation on hydrolysis and aminolysis behaviors of surface-modifiable liposome To 0.4 ml of surface-modifiable liposomes, in which Long-Chain Active Amide I-1 (in formula (I), $R_1=C_{17}H_{35}$, $R_2=R_3=H$, $X=Y=S$) prepared in the same manner as the one described in Example 1 was embedded, was added 0.1 ml of a borate buffer solution (pH 11, I=1.0). Then the decrease in Long-Chain Active Amide I-1 in the system was monitored by HPLC (column: $C_8$, manufactured by Shiseido Co., Ltd., eluent: $CH_3CN$). Similarly, 0.1 ml of a $4.0 \times 10^{-2}M$ benzylamine phosphate buffer solution (pH 7.5, I=1.0) was added and aminolysis was examined. FIG. 1 shows the results.

As FIG. 1 shows, the hydrolysis of Long-Chain Active Amide I-1 (in formula (I), $R_1=C_{17}H_{35}$, $R_2=R_3=H$, $X=Y=S$) scarcely proceeded in the liposome system at pH 11, while Long-Chain Active Amide I-1 formed an amide together with the amine at pH 7.5.

COMPARATIVE EXAMPLE 1

Determination of the hydrolysis rate and aminolysis rate of benzoic acid active amide or ester 1.5 ml of $3.33 \times 10^{-3}M$ solution of each benzoic acid active amide or ester shown in Table 1 in dioxane was mixed with 3.5 ml of a 0.1M phosphate buffer solution (pH 7.4). Then the decrease in the benzoic acid active amide or ester was monitored by HPLC (column: ODS, eluent: $CH_3CN$—$H_2O$ (0.2% AcOH—$Et_3N$)) to thereby determine the hydrolysis rate. Similarly, the aminolysis rate was determined by using 3.5 ml of a $1.43 \times 10^{-2}M$ glycine methyl ester hydrochloride solution in a phosphate buffer solution (pH 7.3). Table 1 shows the results.

EXAMPLE 12

Process for producing surface-modifiable liposome 15 mg of DPPC and 2.3 mg of Long Chain Active Amide II-2 were dissolved in 5 ml of chloroform. Next, the solvent was distilled off in a rotary evaporator to thereby form a film. The film was dried under reduced pressure and 0.5 ml of $H_2O$ was added thereto. Then it was allowed to stand in a water bath at 60° C. for 1 minute followed by shaking in a vortex mixer for 1 minute. After effecting this procedure thrice, the obtained dispersion was irradiated with ultrasonic waves with the use of a probe-type sonicator (25 W, 3 minutes). Then it was subjected to gel filtration with the use of a Sepharose 4B column to thereby give surface-modifiable liposomes (Tc: 41° C., average particle size: 560 nm).

EXAMPLE 13

Encapsulation test on surface-modifiable liposome

Similar to the procedure of Example 12, a dispersion was treated by using a 200 mM 5,(6)-carboxyfluorescein (5,(6)-CF) in a borate buffer solution (pH 8.5) to thereby prepare liposomes in which 5,(6)-CF was encapsulated (average particle size: 300 nm).

EXAMPLE 14

Process for producing surface-modifiable liposome and encapsulation test thereon 30 mg of DPPC and 2 mg of Long Chain Active Amide II-1 were dissolved in 15 ml of chloroform. Then the procedure of Example 12 was repeated to thereby give surface-modifiable liposomes (Tc: 41° C., average particle size: 220 nm). Subsequently, liposomes in which 5,(6)-CF was encapsulated were prepared by using 200 mM 5,(6)-CF in a phosphate buffer solution (pH 7.4) (average particle size: 210 nm).

TABLE 1

| Active amide or ester | Hydrolysis k pH7.4(Min$^{-1}$) | t½ | Aminolysis kobs(Min$^{-1}$) | k(M$^{-1}$.Min$^{-1}$) | t½ |
|---|---|---|---|---|---|
| Ph–C(=O)–N(thiazolidine-2-thione) | $7.6 \times 10^{-4}$ | 15 h | $2.3 \times 10^{-2}$ | 8 | 30 Min |
| Ph–C(=O)–O–N(succinimide) | $2.2 \times 10^{-3}$ | 5 h | $7.7 \times 10^{-2}$ | 25 | 9 Min |
| Ph–C(=O)–O–Ph | —*1 | —*1 | —*1 | —*1 | —*1 |

*1 The reaction did not proceed.

These results indicate that a long-chain active amide having thiazolidine-2-thione as an eliminating group is superior in stability in water to N-hydroxysuccinimide ester which has been frequently used in fixation and aminolysis and that the long-chain active amide would selectively react with an amino group.

EXAMPLE 15

Process for producing surface-modifiable liposome and encapsulation test thereon 30 mg of Egg PC and 2 mg of Long-Chain Active Amide II-8, were dissolved in 15 ml of chloroform. Then the procedure of Example 12 was repeated to thereby give surface-modifiable liposomes (average particle size: 120 nm). Subsequently, liposomes in which 5,(6)-CF was encapsulated were prepared by the same method as the one described in Example 14.

EXAMPLE 16

Process for producing surface-modifiable liposome and encapsulation test thereon 30 mg of DPPC and 3 mg of Long-Chain Active Amide II-9 were dissolved in 25 ml of chloroform. Then the procedure of Example 12 was repeated to thereby give surface-modifiable liposomes (average particle size: 150 nm). Subsequently, liposomes in which 5,(6)-CF was encapsulated were prepared by the same method as the one described in Example 14.

EXAMPLE 17

Process for producing benzylamine-fixed surface-modified liposome

To 0.4 ml of a dispersion of surface-modifiable liposomes in a phosphate buffer solution (pH 7.5), which was produced in the same manner as the one described in Example 12 by using Long-Chain Active Amide II-1 (concentration: $4 \times 10^{-4}$M), was added 0.1 ml of a $4 \times 10^{-2}$M benzylamine in a phosphate buffer solution (pH 7.5). Then the mixture was allowed to stand at 25° C. for 12 hours. As a result, benzylamine-fixed surface-modified liposomes on which benzylamine was fixed on 50% of the long-chain active amide in the liposome membrane were obtained.

EXAMPLE 18

Process for producing peptide-fixed surface-modified liposome

To 0.4 ml of a dispersion of surface-modifiable liposomes in a phosphate buffer solution (pH 7.5), which was produced in the same manner as the one described in Example 17 by using Long-Chain Active Amide II-1 (concentration: $4 \times 10^{-4}$M), was added 0.1 ml of a $4 \times 10^{-2}$M peptide (Ser-Gly-Ala) in a phosphate buffer solution (pH 7.5). Then the mixture was allowed to stand at 25° C. for 12 hours. As a result, peptide-fixed surface-modified liposomes on which said peptide (Ser-Gly-Ala) was fixed on 38% of the long-chain active amide II-1 in the liposome membrane were obtained.

EXAMPLE 19

Process for producing protein-fixed surface-modified liposome

The procedure of Example 12 was repeated by using 15 mg of DPPC, 1.0 mg of Long-Chain Active Amide II-2 and a PBS solution to thereby give surface-modifiable liposomes. These liposomes were sized with an extruder by using a micropore filter (0.2 μm) at 50° C. Then the dispersion was ultracentrifuged (10,000 rpm, 15 minutes) to thereby sediment the liposomes.

To the liposomes thus sedimented, was added 3 ml of a phosphate buffer solution. To a 1 ml portion of the mixture thus obtained, was added 1 ml of a 1 mg/ml human IgG solution in PBS followed by allowing to stand at 25° C. for 12 hours. Then it was ul-tracentrifuged with the use of a PBS solution. Thus protein-fixed surface-modified liposomes, on which said protein (human IgG) was fixed, were obtained.

EXAMPLE 20

Process for producing peptide-fixed surface-modified liposome

To 1 ml of a dispersion of surface-modifiable liposomes in which Long-chain Active Amide II-8 prepared in the same manner as the one described in Example 15, was embedded, was added 1 ml of an aqueous solution of a peptide (Ser-Gly-Ala) followed by allowing to stand at 25° C. for 12 hours. Then the liposome faction was collected by gel filtration to thereby give liposomes on which said peptide (Ser-Gly-Ala) was fixed were obtained.

EXAMPLE 21

Production of saccharide-fixed modified liposomes

In accordance with a method reported by Nagao et al. (Tetrahedron Lett., 21, 841 (1980)), N-tetradecanoyl glucosamine (IV) was obtained.

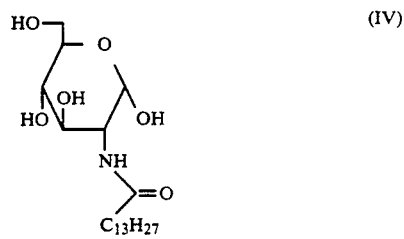
(IV)

1 mg of N-tetradecanoyl glucosamine and 15 mg of DPPC were dissolved in 5 ml of a solvent mixture (methanol/chloroform = 1/1 by volume). Next, the solvent was distilled with a rotary evaporator and thus a film was formed. After drying under reduced pressure, 3 ml of a PBS solution was added to the film. Then it was allowed to stand on a water bath at 60° C. for 1 minute followed by shaking in a vortex mixer for 1 minute. After effecting this procedure thrice, the obtained dispersion was irradiated with ultrasonic waves with the use of a probe-type sonicator (25 W, 10 minutes). Then it was subjected to gel filtration with the use of a Sepharose 4B column to thereby give modified liposomes on which said saccharide (glucosamine) was fixed.

EXAMPLE 22

Observation on hydrolysis and aminolysis behaviors of surface-modifiable liposome To 0.4 ml of surface-modifiable liposomes, in which Long-Chain Active Amide II-1 prepared in the same manner as the one described in Example 12 was embedded, was added 0.1 ml of a borate buffer solution (pH 11, I=1.0). Then the decrease in Long-Chain Active Amide I-1 in the system was monitored by HPLC (column: $C_8$, manufactured by Shiseido Co., Ltd., eluent: $CH_3CN$). Similarly, 0.1 ml of a $5.0 \times 10^{-2}$M benzylamine phosphate buffer solution (pH 7.5, I=1.0) was added and aminolysis was examined. The results were about the same as those shown in FIG. 1.

It was apparent from the results that the hydrolysis of Long-Chain Active Amide II-1 scarcely proceeded in the liposome system at pH 11, while Long-Chain Active Amide II-1 formed an amide together with the amine at pH 7.5.

As described above, the present invention makes it possible to produce surface-modified liposomes on the surface of which various substrates are fixed by simple procedures under mild conditions. Furthermore, the long-chain active amide used in the present invention is superior in stability in water to N-hydroxysuccinimide ester, which has been frequently used fixing a substrate on a liposome (for example, in SPDP method), and has a high suitability for various modified or modifiable liposome commercial applications.

While the invention has been described in detail and with reference to specific examples thereof, it will be apparent to one skilled in the art that various changes and modifications can be made therein without departing from the spirit and scope thereof.

What is claimed is:

1. A surface-modifiable liposome comprising a compound represented by formula (I) or (II):

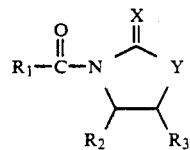  (I)

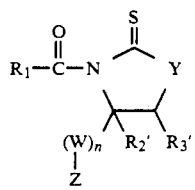  (II)

and a lipid capable of forming a liposome; wherein
   $R_1$ represents a hydrophobic group; $R_2$ and $R_3$ each represents an organic group or a hydrogen atom; $R_2$ and $R_3$ optionally combine with each other to form a double bond or a ring; X and Y each represents an oxygen atom or a sulfur atom; $R_2'$ and $R_3'$ each represents a hydrogen atom or an organic group; W represents a linking group; n represents 0 or 1; and Z represents a hydrophilic group.

2. A surface-modifiable liposome as claimed in claim 1, wherein
   $R_1$ represents a straight-chain alkyl group having carbon atoms of 8 or more or a radical represented by one of formulae ($R_1$-I) to ($R_1$-IV):

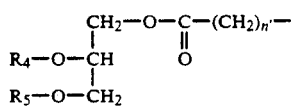  ($R_1$-I)

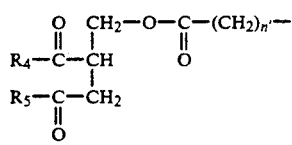  ($R_1$-II)

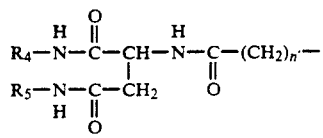  ($R_1$-III)

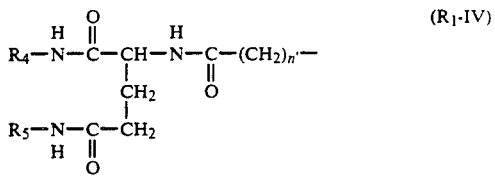  ($R_1$-IV)

wherein
   $R_4$ and $R_5$ each represents an alkyl group having 1 to 22 carbon atoms and n' represents an integer of from 1 to 3.

3. A surface-modifiable liposome as claimed in claim 1, wherein $R_2$ and $R_3$ in formula (I) each represents a hydrogen atom, $-CH_3$, $-CH_2CH_3$, $-OH$, $-COOH$, $-COOCH_3$, $-CH_2OH$, $-CH_2COOH$, $-CH_2COOCH_3$, $-N^+H_3$, $-N^+(CH_3)_3$, $-CH_2N^+H_3$, $CH_2N^+(CH_3)_3$, $-SO_3^-$, or $-CH_2SO_3^-$.

4. A surface-modifiable liposome as claimed in claim 1, wherein X and Y in formula (I) both represent a sulfur atom.

5. A surface-modifiable liposome as claimed in claim 1, wherein $R_2'$ and $R_3'$ in formula (II) each represents a hydrogen atom, an alkyl group, a cycloalkyl group, an alkenyl group, an alkynyl group, an alkyl group having 1 to 5 carbon atoms which is substituted by 1 to 3 halogen atoms, a cyano group, a halogen atom, a nitro group, an alkoxy group, an alkenoxy group, an alkynoxy group, an aryloxy group, an alkoxycarbonyl group, an aryloxycarbonyl group, an alkoxycarbonylthio group, an alkoxycarbonylamino group, a dialkylamino group, an alkylcarbonylamino group, an alkylcarbonyl group, a carbamoyl group, an alkylaminocarbonylamino group, an alkylaminocarbonyloxy group, an alkylaminocarbonylthio group, an alkylsulfinyl group, an arylsulfonyl group or an alkylthio group.

6. A surface-modifiable liposome as claimed in claim 1, wherein Z in formula (II) represents a dialkylamino group, a trialkylammonium group, a sulfo group or dissociated form thereof.

7. A surface-modifiable liposome as claimed in claim 1, W in formula (II) represents $-(CH_2)_m-$, $-(CH_2)_m-CO-$, $-(CH_2)_m-SO_2-$, or

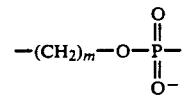

wherein m represents an integer of 0 to 3.

8. A process for producing a surface-modified liposome comprising adding a substrate having at least one of an amino group and a thiol group or a substrate having at least one of amino group and thiol group dissolved in an organic solvent, water or a buffer to a dispersion of the surface-modifiable liposome claimed in claim 1 and water or a buffer.

9. A process for producing a surface-modified liposome as claimed in claim 8, wherein the molar ratio of the compound represented by formula (I) or (II) to all of the materials capable of forming liposomes is from 1 to 50%;

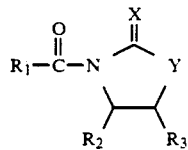

(I)

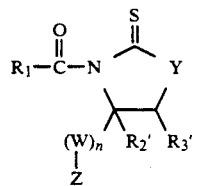

(II)

wherein $R_1$ represents a hydrophobic group; $R_2$ and $R_3$ each represents an organic group or a hydrogen atom; $R_2$ and $R_3$ optionally combine with each other to form a double bond or a ring; X and Y each represents an oxygen atom or a sulfur atom; $R_2'$ and $R_3'$ each represents a hydrogen atom or an organic group; W represents a linking group; n represents 0 or 1; and Z represents a hydrophilic group.

10. A process for producing a surface-modified liposome comprising mixing a substrate derivative comprising at least one compound represented by formula (I) or (II) as claimed in claim 1 bound to a substrate having at least one of an amino group and a thiol group, obtained by adding the substrate having at least one of an amino group and a thiol group to the at least one compound represented by formula (I) or (II) as claimed in claim 1 in an organic solvent, water or a buffer, with a lipid capable of forming a liposome.

11. A process for producing a surface-modified liposome as claimed in claim 10, wherein the molar ratio of materials capable of forming liposomes to the substrate derivative is from 1 to 50%.

* * * * *